United States Patent [19]
Dromard et al.

[11] Patent Number: 5,989,524
[45] Date of Patent: Nov. 23, 1999

[54] SILICA COMPATIBLE WITH FLAVORS, PROCESS FOR ITS PREPARATION AND DENTIFRICE COMPOSITIONS CONTAINING IT

[75] Inventors: Adrien Dromard, Lyons; Jean-Francois Viot, Irigny, both of France

[73] Assignee: Rhodia Chimie, Courbevoie, France

[21] Appl. No.: 08/896,349

[22] Filed: Jul. 18, 1997

[30] Foreign Application Priority Data

Jul. 23, 1996 [FR] France .................................. 96 09202

[51] Int. Cl.$^6$ ............................. A61K 7/16; A61K 7/18; C01B 33/12
[52] U.S. Cl. ............................ 424/49; 423/335; 423/338; 423/339; 424/52
[58] Field of Search .................................... 423/335, 338, 423/339; 424/49, 52

[56] References Cited

U.S. PATENT DOCUMENTS

| | | | |
|---|---|---|---|
| 4,110,083 | 8/1978 | Benedict | 51/295 |
| 4,157,387 | 6/1979 | Benedict | 424/54 |
| 4,340,583 | 7/1982 | Wason | 424/52 |

FOREIGN PATENT DOCUMENTS

| | | | |
|---|---|---|---|
| 0 275706 | 7/1988 | European Pat. Off. | A61K 7/16 |
| WO 93/23007 | 11/1993 | WIPO | A61K 7/22 |
| WO 94/06868 | 3/1994 | WIPO | C09C 1/30 |

OTHER PUBLICATIONS

French Preliminary Search Report.

*Primary Examiner*—Peter O'Sullivan
*Attorney, Agent, or Firm*—John Daniel Wood

[57] ABSTRACT

Silica compatible with flavors, exhibiting, at an RP/DA abrasivity lower than or equal to 10, a compatibility with flavors which is higher than 10% and, at an RP/DA abrasivity higher than 10, a compatibility with flavors of at least 30%. Process for the preparation of flavor-compatible silica by treating the surface of a silica originating from the reaction of an alkali metal silicate with an inorganic or organic acidic agent, the silica being in dry form or in an aqueous suspension, with the aid of an organic compound capable of developing hydrogen bonds or ionic bonds with, respectively, the Si—OH silanol groups or the SiO$^-$ anionic groups at the surface of the said silica to be treated, the said treated silica being subsequently, if necessary, isolated and/or washed and/or dried. Use in dentifrice compositions and dentifrice compositions including the said silica.

22 Claims, No Drawings

SILICA COMPATIBLE WITH FLAVORS, PROCESS FOR ITS PREPARATION AND DENTIFRICE COMPOSITIONS CONTAINING IT

The present invention relates to a silica with improved compatibility with flavours, which can be employed especially as an abrasive and/or thickening agent in dentifrice pastes and gels, to a process for its preparation and to its application as an abrasive and/or thickening agent in dentifrice pastes and gels or other formulations for dental or oral hygiene.

Precipitated silicas and silica gels are widely employed as abrasives in dentifrice pastes. When compared with the other abrasives traditionally employed, such as calcium phosphates or precipitated calcium carbonates, the precipitated silicas and silica gels have the following specific properties and performance:
a high compatibility with therapeutic agents, in particular fluorine, and also with antitartar agents
a finely adjustable refractive index which can range from 1.44 to 1.46, depending on whether precipitated silica or silica gel is involved, allowing their application in translucent gel formulations.

Furthermore, precipitated silicas exhibiting the highest pore volumes and silica gels are employed as thickening agents in dentifrice pastes and gels. They contribute more particularly a high flow threshold and considerably reduce the running of dentifrice products.

Abrasive or thickening precipitated silicas and silica gels are entirely compatible with therapeutic agents and also permit the manufacture of translucent gels.

On the other hand, it is recognized that the presence of precipitated silica or of silica gel in dentifrice formulations alters the recovery of the flavours employed.

It is also known that the source of this alteration in the recovery of flavours lies in the adsorption of the flavour molecules onto the surface of the silica. This adsorption is confirmed with most of the flavours employed in dentifrices.

It has been proposed to minimize the interaction of silicas with flavours by treating the silicas in the finished product state with an alkaline inorganic material (for example sodium hydroxide). A reduction of 2% in the area of the headspace peak of the flavour, measured by gas chromatography, against a reduction of 20% in the case of an untreated silica, has been shown (WO 94/06868).

It is also known to coat the surface of abrasive silicas with a cationic polymer, to make them less adsorbent towards therapeutic cationic agents (US-A-4 157 387).

A first subject-matter of the invention consists of a silica with improved compatibility with flavours, characterized in that, at an RP/DA ("Rhône-Poulenc Dentine Abrasion") abrasivity lower than or equal to 10, it exhibits a compatibility with flavours which is higher than 10%, preferably higher than 15% and, at an RP/DA ("Rhône-Poulenc Dentine Abrasion") abrasivity higher than 10, a compatibility with flavours of at least 30%, preferably higher than 50%.

The compatibility of the silica with regard to flavours is measured by headspace chromatography with the aid of a Varian 3400 gas phase chromatograph, in the following manner:
The flavour chosen is L-carvone, which constitutes an important part of traditional elementary flavours; this is placed directly in contact with the silica to be tested in a headspace flask. After closing the flask and obtaining thermodynamic equilibrium between the solid phase and the surrounding vapour phase, with the aid of a constant temperature bath at 50° C., 1 ml of vapour phase is taken and injected into the column of the chromatograph.

The chromatogram obtained shows the composition of the vapour phase; the area of the main chromatographic peak of L-carvone is measured.

A reference measurement is performed in the same conditions, the silica being replaced with dicalcium phosphate (Victor DF from Rhône-Poulenc), known for its good compatibility with flavours.

The compatibility of the silica with flavours, CF, is given by the following equation:

$$CF = \frac{\text{area of the peak corresponding to L-carvone in the presence of silica}}{\text{area of the peak corresponding to L-carvone in the presence of dicalcium phosphate}} \times 100$$

The evaluation of the RP/DA abrasivity is carried out according to a test which allows the relative abrasivity of an abrasive or of a dental paste at the end of a cycle of brushing on previously polished human dentine to be quantified in relation to a reference silica powder of dental grade; the absolute abrasivity of the powder or of the paste tested is determined with the aid of a Rank Taylor Hobson Talysurf 10 profilometer, which measures the mean depths of wear of the dentine after brushing. A series of human teeth is coated with polymethyl methacrylate resin and then polished with the aid of a polisher until the dentine appears.

Two side regions are isolated on the test pieces by bonding with transparent adhesive; during the profilometric measurement the protected portions of the dentine will form reference surfaces from which the mean depths of the wear mark is measured.

Brushing of the surfaces is carried out with the aid of an abrasimeter equipped with support cells and fitted with toothbrushes; the brushing conditions are 1500 back-and-forth strokes; each tested product is preceded and followed by a cycle of brushing and of measurements with the reference abrasive.

The dispersions of powder or paste to be tested are prepared according to the procedure recommended by the American Dental Association and described by John J. Hefferen in J. Dental Research, vol. 55, No. 4, 563–573, 1976.

Insofar as the powders are concerned (those to be tested and those for reference), 80 g of powder are dispersed with the aid of a Rayneri stirrer in a medium consisting of glycerol (10%), carboxymethyl cellulose (0.5%) and distilled water (89.5).

Insofar as the pastes are concerned, 200 g of paste are dispersed with the aid of a Rayneri stirrer in 320 ml of distilled water.

Four profilometric measurements are carried out per dentine in a region situated towards a defined edge of the sample; the test of the same product on 4 dentines provides 16 values in all for the calculation of the mean depth of wear Hm.

The relative RP/DA abrasivity (%) of the tested product is given by the following relationship $$RP/DA\ (\%) = \frac{Hm\ \text{obtained with the test product}}{Hm\ \text{obtained with the reference product}} \times 100$$

the value 118 corresponding to the RDA abrasivity of the reference silica, the RDA (Radioactive Dentine Abrasion) abrasivity being measured according to the method described by J. J. Hefferen in Journal of Dental Research, vol. 55(4), page 563, 1976.

The silica forming the subject-matter of the invention may be equally well a precipitated silica or a silica gel.

It can be obtained according to a process constituting a second subject-matter of the invention, a process characterized in that the surface of a silica originating from the reaction of an alkali metal silicate with an inorganic or organic acidic agent, the silica being in dry form or in an aqueous suspension, is treated with the aid of an organic compound capable of developing hydrogen bonds or ionic bonds with, respectively, the Si—OH silanol groups or the SiO$^-$ anionic groups at the surface of the said silica to be treated, the said treated silica being subsequently, if necessary, isolated and/or washed and/or dried.

The preparation of precipitated silica or of silica gel by reaction of an alkali metal silicate with an inorganic or organic acidic agent is an operation which is well known per se.

According to the conventional scheme, the said silicate is preferably used in the form of an aqueous solution of silicate of alkali metal M (the metal M denoting especially sodium or potassium) with an $SiO_2/M_2O$ ratio of the order of 2 to 4; this solution generally has an $SiO_2$ concentration of the order of 30 to 350 g/l.

The acidic agent may be any strong inorganic or organic acid such as sulphuric acid, nitric acid, hydrochloric acid, acetic acid, formic acid, carbonic acid and the like; it is generally also used in aqueous solution at a concentration of the order of 60 to 400 g/l in the case of sulphuric acid.

This operation is carried out in most cases at a temperature of the order of 80 to 100° C., sodium silicate with an $SiO_2/Na_2O$ ratio of the order of 2 to 4 being used as silicate and sulphuric acid as acidic agent.

The respective quantities of sodium silicate and sulphuric acid are adjusted so as to maintain the pH of the reaction mixture for forming silica at a substantially constant value of the order of 2 to 10, more precisely of the order of 2 to 5 for preparing a silica gel and of 5 to 10 for preparing a precipitated silica.

The reaction slurry obtained is next filtered and washed, generally with water, and then the filter cake recovered is dried and optionally ground.

An advantage of the invention consists in that, if the treatment is carried out on a silica suspension, it can take place in the course of the actual process for preparing the silica.

According to a first embodiment of the invention the silica to be treated is in the dilute suspension consisting of the slurry originating directly from the reaction of the alkali metal silicate with the inorganic or organic acidic agent. This reaction slurry consists of a suspension of silica in a solution of salt (most generally a solution of sodium sulphate).

The silica concentration, expressed on dry basis, in the said suspension can range from 10 to 150 g, generally from 40 to 80 g of $SiO_2$ per liter of salt solution.

According to this first embodiment of the invention the treatment with the organic compound can be carried out by bringing the reaction slurry and the organic treatment compound into contact, with mechanical stirring, at a temperature of the order of 20° C. to 100° C., at a pH of the order of 1 to 10, preferably of the order of 3 to 6.

The reaction slurry thus treated is next separated by filtration, by any known means, and then washed with water; the silica cake obtained can, optionally after crumbling, be dried next in order to have a moisture content (measured at 105° C. according to ISO standard 787/2) lower than 50%, preferably lower than 10%, very particularly of the order of 4 to 8%, and then ground if necessary by any means until the finished product of desired particle size is obtained.

According to a second embodiment of the invention the silica to be treated is in the concentrated suspension consisting of the silica cake originating from the filtration, with optional washing with water, of the reaction slurry formed by reaction of the alkali metal silicate with the inorganic or organic acidic agent.

The stage of filtration of the reaction slurry may be carried out by any known means, for example with the aid of a filter press, of a vacuum filter, etc. The cake is optionally washed, generally with water. The said cake consists of a suspension of silica in water which may contain a small quantity of residual salt.

The silica concentration, expressed on dry basis, in the said cake is generally such that the said cake has a solids content (measurement of the loss on ignition at 1000° C., according to ISO standard 3262/11) of the order of 10 to 45%.

The treatment, with the organic compound, of the silica present in the filter cake can be carried out by bringing the filter cake and the organic treatment compound into contact, with mechanical stirring, at a temperature of the order of 10° C. to 80° C., preferably of the order of 15° C. to 40° C., at a pH of the order of 3 to 10, preferably of the order of 5 to 8.

The treated silica cake obtained may, optionally after crumbling, be dried next, in order to have a moisture content lower than 50%, preferably lower than 10%, preferably of the order of 4 to 8%, and then may be ground if necessary by any means until the finished product of desired particle size is obtained.

According to a third embodiment of the invention the silica to be treated with the organic compound is a silica in dry form which may be a precipitated silica or a silica gel exhibiting a moisture lower than 50%, preferably lower than 10% preferably of the order of 4 to 8%, obtained by drying, optionally after crumbling, of the silica cake originating from the filtration with washing of the reaction slurry formed by reaction of the alkali metal silicate with the inorganic or organic acidic agent. The treatment with the organic compound may be performed by spraying the organic treatment compound onto the surface of the dry silica, this spraying operation being preferably carried out either on the said preground silica or during an operation of grinding the said silica.

The said organic compound to be sprayed may be in the form of an aqueous solution containing of the order of 0.5 to 10% of active substance, it being possible for the quantity of solution absorbed to represent from 0.1 to 4 times the weight of silica concerned; the treated silica is next optionally dried to obtain the intended dryness; this drying operation may be carried out in a fluidized bed.

It is very particularly advantageous to make use of this third embodiment as a preliminary to the preparation of the dentifrice formulation. The treated silica can then not be dried.

The compound to be sprayed may also be sprayed in melted form if it is not naturally liquid at the temperature of the operation.

According to a fourth embodiment of the invention the silica to be treated is in a concentrated suspension obtained by redispersion, in water, of a dry silica prepared beforehand, it being possible for the dry silica to be a precipitated silica or a silica gel. The silica concentration, expressed on dry basis, in the said suspension may be such that the latter has a solids content of the order of 10 to 45%.

The treatment with the organic compound of the silica present in the said suspension may be carried out by bringing the suspension and the organic treatment compound into contact, with mechanical stirring, at a temperature of the order of 10° C. to 80° C., preferably of the order of 15° C. to 40° C., at a pH of the order of 3 to 10, preferably of the order of 5 to 8.

The treated silica suspension obtained may, optionally after crumbling, be dried next, in order to have a moisture content lower than 10%, preferably of the order of 4 to 8%, and then ground if necessary by any means until the finished product of desired particle size is obtained.

According to a fifth embodiment of the invention the silica to be treated is in a concentrated suspension obtained by redispersion, in an aqueous solution of the organic treatment compound, of the dry silica prepared beforehand, it being possible for this dry silica to be a precipitated silica or a silica gel; the treatment with the organic compound of the silica present in the said suspension may be carried out with mechanical stirring at a temperature of the order of 10° C. to 80° C., preferably of the order of 15° C. to 40° C., at a pH of the order of 3 to 10, preferably of the order of 5 to 8.

It is very particularly advantageous to make use of the fourth and fifth embodiment as a preliminary to the preparation of the dentifrice formulation; the treated silica can then not be dried.

Whichever the embodiment chosen, the optional operations of grinding can be carried out by any means (with the aid of hammer mills, micronization etc.), to a particle size of the order of 1 to 60 $\mu$m, preferably of the order of 3 to 20 $\mu$m.

The following nonionic or cationic organic compounds may be mentioned among the organic compounds capable of treating the silica according to the invention to improve its compatibility with flavours polyethylene glycols
polyvinyl alcohols
polyvinylpyrrolidones
polyalkoxylated polydimethylsiloxanes (Rhône-Poulenc Silicone Copolyol 10 646)
cinnamic acid
para-hydroxybenzoic acid and its esters, like methyl para-hydroxybenzoate
cationic guars (Rhône-Poulenc Jaguar C17 and C162)
the polyquaternary ammonium ionenes described in U.S. Pat. No. 4,157,388 (Rhône-Poulenc Polyquaternium-2 or Mirapol A-15)
polymers derived from epichlorohydrin and dimethylamine and those derived from epichlorohydrin and imidazole, like Rhône-Poulenc ELC and Glokill PQ.

The quantities of organic treatment compound which are used according to the invention may be of the order of 0.1 to 30 parts by weight, preferably of the order of 0.5 to 25 parts by weight, per 100 parts by weight of silica, expressed as solid material.

The nature of the organic compound to be used is a function in particular of the method of treatment which is chosen and of the pH of treatment when the latter is performed in aqueous medium.

Thus, silica in an aqueous suspension of pH lower than 6, for example silica in suspension in an aqueous concentrated salt solution (for example sodium sulphate), exhibits a high density of SiOH silanol functional groups at its surface. The organic compounds capable of treating the surface of this silica most favourably are then nonionic water-soluble organic compounds, with formation predominantly of hydrogen bonds.

Silica in an aqueous suspension of pH of the order of 6 to 8, for example silica in suspension in an aqueous solution which is free from salt or highly dilute in salt, exhibits a high density of SiO$^-$ anionic functional groups at its surface. The organic compounds capable of treating the surface of this silica most favourably are then cationic water-soluble organic compounds, with formation predominantly of ionic bonds; however, nonionic organic compounds can also be chosen, because they are capable of forming a sufficient number of hydrogen bonds.

Washed and dried silica of pH of the order of 6 to 8 exhibits a high density of SiO$^-$ anionic functional groups at its surface. The organic compounds capable of treating the surface of this silica most favourably are then cationic organic compounds, with formation predominantly of ionic bonds; however, nonionic organic compounds can also be chosen because they are capable of forming a sufficient number of effective hydrogen bonds.

The silica forming the subject-matter of the invention exhibits a high compatibility with flavours, especially with the flavours present in dentifrices.

Among the flavours compatible with the treated silicas according to the invention there may be mentioned very particularly the elementary flavours commonly employed in dentifrices, such as menthol, L-carvone, methyl salicylate, cinnamaldehyde, eugenol, anethol, terpenes (limonene, pinene) etc., essential oils such as peppermint or spearmint extracts, extracts of chinese anise-tree, clove, cinnamon, eucalyptus, etc.

The silica of the invention, additionally retaining
a high compatibility with therapeutic agents, fluorine in particular, and with antitartar agents,
considerable abrasive and/or thickening properties, and
a refractive index of the order of 1.44 to 1.46, is very particularly adapted to the formulation of dentifrice pastes, of dentifrice gels or of liquid dentifrices.

Besides the silica of the invention and the abovementioned flavours, these dentifrice compositions may include other usual ingredients, in particular other, water-insoluble inorganic abrasive agents, thickening agents, moisturizers, and the like. Other abrasive agents which may be mentioned in particular are calcium carbonate, hydrated alumina, bentonite, aluminium silicate, zirconium silicate and sodium, potassium, calcium and magnesium metaphosphates and phosphates. The total quantity of abrasive powder(s) may constitute of the order of 5 to 50% of the weight of the dental composition.

Among the thickening agents there may be mentioned most particularly the thickening silicas in a quantity of the order of 1 to 15% of the weight, xanthan gum, guar gum, carrageenans, cellulose derivatives and alginates, in a quantity that can range up to 5% of the weight of the said composition, etc.

Among the moisturizing agents there may be mentioned, for example, glycerol, sorbitol, polyethylene glycols, polypropylene glycols and xylitol, in a quantity of the order of 2 to 85%, preferably of the order of 10 to 70% of the weight of dentifrice composition, expressed on dry basis. These dentifrice compositions may additionally comprise surface-active agents, detergent agents, colourants, bactericides, fluorine derivatives, opacifiers, sweeteners, antitartar and antiplaque agents, whitening agents, sodium bicarbonate, antiseptics, enzymes, etc.

The following examples are given by way of illustration.
Measurement of the compatibility with regard to sodium fluoride NaF The principle of the measurement consists in leaving the silica to be tested in contact with a solution of sodium fluoride of known concentration for 24 hours at 37° C.

The quantity of fluoride present in the liquid medium obtained by centrifuging is measured by ionometry.

Procedure

The silica to be tested is suspended at a concentration of 20% in an aqueous solution of NaF at a concentration of 1250 ppm, expressed as fluoride $F^-$; the $F^-/SiO_2$ ratio is therefore 5000 ppm. The contact is maintained for 24 h at 37° C. with stirring. The suspension is centrifuged. The supernatant is diluted 20-fold with water. The $F^-$ concentration is measured by ionometry and compared with the concentration of the initial solution which has had no contact with silica. The quantity of $F^-$ adsorbed by the silica (expressed in parts of $F^-$ per million of silica) is calculated.

Measurement of the compatibility with regard to amine fluorides

The principle of the measurement consists in leaving the silica to be tested in contact with a solution of amine fluoride of known concentration for 24 hours at 37° C.

The quantity of amine fluoride present in the liquid medium obtained by centrifuging is measured by turbidimetry by a reaction with an anionic reactant (formation of micelles between the amine fluoride and the anionic reactant used for the test).

Procedure

Turbidimetry measurement on the sample solution 6 g of silica are brought into contact in 24 g of a standard solution of ADHF containing 1.65% by weight of bis(hydroxyethyl)aminopropyl-N-(hydroxyethyloctadecylamine) dihydrofluoride in 1,2-propanediol at a pH of 5, for 24 hours at 370C with magnetic stirring. After centrifuging, 2 g (test sample weight P) of supernatant are taken, filtered and treated by the addition of 5 g of demineralized water.

The quantity of amine fluoride present in the liquid medium is evaluated by turbidimetry by measuring the volume of Aerosol OT (aqueous solution containing 1.9 g/l of sodium dioctylsulfosuccinate, marketed by Touzard et Matignon), for dropping the potential from 1000 to 50 mV (micelle formation).

Turbidimetry measurement on the standard solution

Turbidimetry measurements are carried out in the same way, with the aid of Aerosol OT, on standard solutions containing M grams of standard solution of ADHF, i.e. 0.5 g, 1 g and 2 of standard ADHF solution respectively, in 49.5 g, 49 g and 48 g of demineralized water, respectively (standard solutions corresponding to compatibilities of 25, 50 and 100%).

The solution adopted as standard is that in the case of which the volume Vn of Aerosol OT poured is closest to the volume V poured in the case of the sample solution. The compatibility of the test silica for amine fluoride is given by the formula Compatibility in $\% = [(V \times M)/(Vn \times P)] \times 100$ Measurement of the compatibility with regard to cetylpyridinium chloride (CPC)

8 g of silica to be tested are introduced into 40 g of an aqueous solution (demineralized water) containing 1.19% by weight of CPC, in order to obtain a suspension containing 1% by weight of CPC.

The pH of the suspension is adjusted to 6 by adding 2N HCl or NaOH.

The suspension is left for 24 h at 37° C. with stirring; it is next centrifuged for 30 minutes at 10 000 revolutions/minute and the supernatant is then filtered on a 0.22-μm filter.

The filtrate obtained is diluted (1 g of filtrate per 99 g of water) to measure its UV absorbance at 259 nm. A control solution of CPC is obtained according to the same process, without introduction of silica. The compatibility of the test silica for cetylpyridinium chloride is given by the formula Compatibility in $\%$ = O.D. of the test/O.D. of the control $\times 100$ O.D. denoting the optical density of the solution at 259 nm.

EXAMPLE 1

A reaction slurry "B", the characteristics of which are given below, is prepared from
an aqueous solution of sodium silicate of $SiO_2/Na_2O$ molar ratio of 3.6, which has an $SiO_2$ concentration of 136 g/l. and an aqueous solution containing 80 g/l of sulphuric acid.

The temperature at the end of precipitation is of the order of 90° C.

The slurry "B" is next filtered and washed with the aid of a rotary vacuum filter.

The silica cake obtained is next converted into fluid merely by mechanical action; the cake obtained "G" is atomized by means of a turbine atomizer; the dried product is finally ground; a silica "S" is obtained. The characteristics of the products corresponding to the various stages are given in Table 1. The DOP oil uptake is determined according to ISO standard 787/5 by using dioctyl phthalate. The weight-median diameter $d_{50}$ of the silica particles was determined with the aid of a Sympatec Helos instrument. This instrument applies the Fraunhofer diffraction principle and uses a low-power He/Ne laser. The sample is predispersed by the application of ultrasonics in water for 30 seconds to obtain an aqueous suspension.

EXAMPLE 2

A fraction of the slurry "B" is taken at the end of precipitation.

This fraction is next divided into two portions "B1" and "B2" which are treated as follows:

treatment of "B1"

an aqueous solution of PVP (polyvinylpyrrolidone K 30 from International Specialty Polymers) at a concentration of 15% by weight is introduced slowly with stirring into the slurry "B1" maintained at its temperature of preparation, in a sufficient quantity to obtain a ratio of PVP to silica of 2%;

treatment of "B2"

Silicone Copolyol 10646 (10646-Rhône-Poulenc polyalkoxylated polyorganosiloxane) is introduced slowly with stirring into the slurry "B2" maintained at its temperature of preparation, in sufficient quantity to obtain a ratio of Silicone Copolyol 10646 to silica of 2%;

Each treated slurry is next filtered and washed with water on a cloth. The filter cake is recovered and dried with a laboratory spray-drier. The treated silicas "SB1" and "SB2" are thus obtained. The characteristics of these silicas thus treated appear in Table 1.

EXAMPLE 3

A sample of filter cake "G" is taken.

This fraction is next divided into two portions "G1" and "G2", which are treated as follows:

treatment of "G1"

Mirapol A15®, aqueous solution at a concentration of 65% by weight of cationic polymer marketed by Rhône-Poulenc, is added with strong stirring to the filter cake "G1", at ambient temperature, in a quantity corresponding to a ratio cationic polymer/silica, expressed as dry materials, of 0.8%. Stirring is maintained for another 5 minutes.

treatment of "G2"
Mirapol A15®, aqueous solution containing 65% by weight of cationic polymer marketed by Rhône-Poulenc, is added with strong stirring to the filter cake "G2", at ambient temperature, in a quantity corresponding to a ratio cationic polymer/silica, expressed as dry materials, of 1.2%. Stirring is maintained for another 5 minutes.
Once treated, the cakes "G1" and "G2" are dried with the aid of a laboratory spray-drier. The treated silicas "SG1" and "SG2" are thus obtained.
A control silica "SG0" is obtained by following the same procedure without adding polymer.
The characteristics of these silicas, thus treated, appear in Table 3.

EXAMPLE 4

Silica "S" the characteristics of which are given in Table 1, is resuspended in water in proportions such that the solids content at 1000° C. is of the order of 63 to 66%.
This suspension is next divided into three portions "G3", "G4" and "G5", which are treated as follows:
treatment of "G3"
Glokill PQ®, aqueous solution at a concentration of 50% by weight of cationic polymer (derived from epichlorohydrin and dimethylamine) marketed by Rhône-Poulenc, is added with strong stirring to the filter cake "G3", at ambient temperature, in a quantity corresponding to a ratio cationic polymer/silica, expressed as dry materials, of 1%. Stirring is maintained for another 5 minutes.
treatment of "G4"
Glokill ELC®, aqueous solution at a concentration of 50% by weight of cationic polymer (derived from epichlorohydrin and imidazole), marketed by Rhône-Poulenc, is added with strong stirring to the filter cake "G4", at ambient temperature, in a quantity corresponding to a ratio cationic polymer/silica, expressed as dry materials, of 1%. Stirring is maintained for another 5 minutes.
treatment of "G5"
an aqueous solution containing 1% of Jaguar C162, cationic guar marketed by Rhône-Poulenc, is added with strong stirring to the filter cake "G5", at ambient temperature, in a quantity corresponding to a ratio cationic guar/silica, expressed as dry materials, of 1%. Stirring is maintained for another 5 minutes. After treatment the cakes "G3", "G4" and "G5" are dried in a ventilated oven for 18 hours at 120° C. The treated silicas "SG3", "SG4" and "SG5" are thus obtained.
A control silica "SG'0" is obtained by following the same procedure, without adding polymer.
The characteristics of these silicas thus treated appear in Table 4.

EXAMPLE 5

Commercial precipitated silicas "C1", "C2" and "C3", the characteristics of which are given in Table 5, are treated as follows:
The solution of treatment polymer is finely sprayed onto the silica in a Patterson Kelley brand V blender with a total capacity of approximately 10 liters, while being mechanically stirred.
Silica "C1" is divided into three portions "C10" (control), "C11" and "C12".
treatment of "C11"
500 g of this silica are introduced into the blender; 500 g of aqueous solution of PVP at a concentration of 5% by weight are finely sprayed for 6 minutes while the silica is stirred.
After spraying, the silica is still kept in motion for 15 minutes longer.
The silica is next removed from the blender and dried in an oven for 24 hours at 120° C. to remove the excess water. The theoretical final PVP/silica ratio is 5%.
treatment of "C12"
The above operation is repeated with the aid of a solution containing 5% of Silicone Copolyol 10646 as treatment agent.
treatment of "C10"
The above operation is repeated with the aid of 500 g of water without treatment agent.
Silica "C2" is divided into three portions "C20" (control), "C21" and "C22".
treatment of "C21"
1250 g of this silica are introduced into the blender; 536 g of aqueous solution of PVP at a concentration of 4.66% by weight are finely sprayed for 6 minutes while the silica is stirred.
After spraying, the silica is kept in motion for 15 minutes longer.
The silica is next removed from the blender and dried in an oven for 24 hours at 120° C. to remove the excess water. The theoretical final PVP/silica ratio is 2%.
treatment of "C22"
The above operation is repeated with the aid of a solution containing 4.66% of Silicone Copolyol 10646 as treatment agent.
treatment of "C20"
The above operation is repeated with the aid of 536 g of water without treatment agent.
Silica "C3" is divided into two portions "C30" (control) and "C31".
treatment of "C31"
1250 g of this silica are introduced into the blender; 536 g of aqueous solution of PVP at a concentration of 4.66% by weight are finely sprayed for 6 minutes while the silica is stirred.
After spraying, the silica is kept in motion for 15 minutes longer.
The silica is next removed from the blender and dried in an oven for 24 hours at 120° C. to remove the excess water. The theoretical final PVP/silica ratio is 2%.
treatment of "C30"
The above operation is repeated with the aid of 536 g of water without treatment agent.
The characteristics of these silicas thus treated appear in Table 5.

TABLE 1

| characteristics | slurry "B" | cake "G" | silica "S" |
|---|---|---|---|
| pH | 3.4 | 6.3 | 6.5 |
| sulphates (%) | 7.8 | 0.8 | 0.5 |
| moisture | — | — | 6.5 |
| loss on ignition | 93 | 62.4 | 10.3 |
| DOP | — | — | 100 |
| RP/DA | — | — | 100 |
| d50 | 13.4 | 25 | 27.7 |
| CPC compatibility | — | — | 36 |
| NaF compatibility | — | — | 88 |
| amine fluoride compatibility | — | — | 45 |
| flavour compatibility | — | — | 15–20 |

TABLE 2

| characteristics | SB1 | SB2 |
| --- | --- | --- |
| pH | 7.61 | 7.5 |
| sulphates (%) | 0.06 | — |
| moisture | 4.5 | 5.8 |
| loss on ignition | 9.5 | 10.7 |
| d50 | 12.1 | 13.6 |
| CPC compatibility | 82 | 72 |
| NaF compatibility | 92 | 94 |
| AF compatibility | 86 | 84 |
| flavour compatibility | 87 | 66 |

TABLE 3

| characteristics | SG0 | SG1 | SG2 |
| --- | --- | --- | --- |
| pH | 7.0 | 6.3 | 6.2 |
| sulphates (%) | 0.5 | 0.5 | 0.5 |
| moisture | 4.8 | 5.3 | 4.3 |
| loss on ignition | 8.81 | 10.1 | 9.3 |
| d50 | 21 | 27.2 | 31.7 |
| CPC compatibility | 42 | 60 | 65 |
| NaF compatibility | ≈90 | 85 | 83 |
| AF compatibility | 48 | 99 | 98 |
| flavour compatibility | 25 | 47 | 45 |

TABLE 4

| characteristics | SG'0 | SG3 | SG4 | SG5 |
| --- | --- | --- | --- | --- |
| pH | 7.0 | 6.2 | 6.3 | 6.5 |
| sulphates (%) | 1.0 | 0.8 | 0.7 | 0.8 |
| moisture | 0 | 0 | 0 | 0 |
| loss on ignition | 3.12 | 4.3 | 4.4 | 4.3 |
| d50 | 31.2 | 34.6 | 31.8 | 32.7 |
| CPC compatibility | 26 | 36 | 42 | 43 |
| NaF compatibility | 91 | 89 | 84 | 89 |
| FA compatibility | 34 | 58 | 87 | 51 |
| flavour compatibility | 28 | 62 | 54 | 63 |

TABLE 5

| characteristics | C1 | C10 | C11 | C12 | C2 | C20 | C21 | C22 | C3 | C30 | C31 |
| --- | --- | --- | --- | --- | --- | --- | --- | --- | --- | --- | --- |
| pH | 7.3 | 7.6 | 7.9 | 7.5 | 6.6 | 7.0 | 7.4 | 4.3 | 6.9 | 6.8 | 7.2 |
| sulphates (%) | 2.7 | 2.8 | 2.4 | 2.6 | 0.6 | 0.6 | 0.6 | 0.7 | 0.3 | 0.3 | 0.3 |
| moisture | 7.1 | 3.4 | 15.9 | 7.8 | 5.9 | 1.5 | 8.1 | 10.4 | 3.6 | 0.6 | 7.9 |
| loss on ignition | 11.0 | 6.9 | 22.4 | 15.0 | 9.7 | 5.2 | 13.3 | 15.4 | 6.2 | 3.3 | 12.1 |
| DOP | 344 | 236 | 268 | 304 | 90 | 90 | 92 | 88 | 124 | 148 | 116 |
| RP/DA | <10 | <10 | <10 | <10 | 100 | 92 | 66 | 80 | 80 | 80 | 75 |
| d50 | 11 | 12 | 11 | 11 | 8 | 8 | 8 | 7 | 10 | 10 | 10 |
| CPC compatibility | — | — | — | — | 28 | 23 | 64 | 58 | — | 16 | 47 |
| FA compatibility | — | — | — | — | 53 | 52 | 96 | 68 | 15 | 10 | 67 |
| NaF compatibility | 92 | 94 | 94 | 96 | 94 | 96 | 96 | 96 | 95 | 98 | 97 |
| flavour compatibility | 0 | 2 | 16 | 23 | 6 | 3 | 41 | 50 | 1 | 3 | 30 |

What is claimed is:

1. A silica having a compatibility with flavours higher than 10% at an RP/DA abrasivity lower than or equal to 10 and a compatibility with flavours higher than 30% at an RP/DA abrasivity higher than 10.

2. A silica according to claim 1, having a compatibility with flavours higher than 15% at an RP/DA abrasivity lower than or equal to 10 and a compatibility with flavours higher than 50% at an RP/DA abrasivity higher than 10.

3. A process for the preparation of a silica having a compatibility with flavours higher than 10% at an RP/DA abrasivity lower than or equal to 10 and a compatibility with flavours higher than 30% at an RP/DA abrasivity higher than 10 comprising the steps of:

treating the surface of a silica originating from the reaction of an alkali metal silicate with an inorganic or organic acidic agent, the silica being in dry form or in an aqueous suspension, with an organic compound capable of developing hydrogen bonds or ionic bonds with, respectively, the Si—OH silanol groups or the SiO⁻ anionic groups at the surface of the said silica to be treated; and subsequently isolating or washing or drying the said treated silica.

4. A process according to claim 3, wherein the silica to be treated is in a dilute aqueous suspension comprising a slurry originating directly from the reaction of the alkali metal silicate with the inorganic or organic acidic agent.

5. A process according to claim 4, wherein the treatment with the organic compound is carried out by bringing the suspension and the organic compound into contact, with mechanical stirring, at a temperature of about 20° C. to 100° C. and at a pH of about 1 to 10.

6. A process according to claim 5, wherein the pH is about 3 to 6.

7. A process according to claim 3, wherein the silica to be treated is in a concentrated suspension comprising a silica cake originating from the filtration, with optional washing with water, of a reaction slurry formed by reaction of the alkali metal silicate with the inorganic or organic acidic agent.

8. A process according to claim 7, wherein the treatment, with the organic compound, of the silica cake is carried out by bringing the silica cake and the organic compound into contact, with mechanical stirring, at a temperature of about 10° C. to 80° C. and at a pH of about 3 to 10.

9. A process according to claim 8, wherein the temperature is about 15° C. to 40° C. and the pH is about 5 to 8.

10. A process according to claim 3, wherein the silica to be treated with the organic compound is a silica in dry form exhibiting a moisture lower than 50%, obtained by drying, optionally after crumbling, of a silica cake originating from the filtration with washing of a reaction slurry formed by reaction of the alkali metal silicate with the inorganic or organic acidic agent.

11. A process according to claim 10, wherein the treatment with the organic compound is performed by spraying the organic compound onto the surface of the silica.

12. A process according to claim 3, wherein the silica to be treated is in a concentrated suspension obtained by redispersion, in water, of a dry silica prepared beforehand.

13. A process according to claim 12, wherein the treatment with the organic compound of the silica present in the said suspension is carried out by bringing the suspension and the organic compound into contact, with mechanical stirring, at a temperature of about 10° C. to 80° C. and at a pH of about 3 to 10.

14. A process according to claim 13, wherein the temperature is about 15° C. to 40° C. and the pH is about 5 to 8.

15. A process according to claim 3, wherein the silica to be treated is in a concentrated suspension obtained by redispersion, in an aqueous solution of the organic compound, of the silica prepared beforehand.

16. A process according to claim 15, wherein the treatment with the organic compound of the silica present in the said suspension is carried out with mechanical stirring at a temperature of about 10° C. to 80° C. and at a pH of about 3 to 10.

17. A process according to claim 16, wherein the temperature is about 15° C. to 40° C. and the pH is about 5 to 8.

18. A process according to claim 3, wherein the organic compound is a nonionic or cationic, water-soluble organic compound.

19. A process according to claim 18, wherein the organic compound is a polyethylene glycol, a polyvinyl alcohol, a polyvinylpyrrolidone, a polyalkoxylated polydimethylsiloxane, a cinnamic acid, para-hydroxybenzoic acid, an ester of para-hydroxybenzoic acid, a cationic guar, a polyquaternary ammonium ionene, a polymer prepared from epichlorohydrin and dimethylamine or a polymer prepared from epichlorohydrin and imidazole.

20. A process according to claim 19, wherein the quantities of organic compound which are used are about 0.1 to 30 parts by weight, per 100 parts by weight of silica, expressed as solid material.

21. A process according to claim 20, wherein the quantities of organic compound are about 0.5 to 25 parts by weight.

22. A dentifrice composition comprising as abrasive or thickening agent a silica as defined in claim 1.

* * * * *